United States Patent [19]
Morgan et al.

[11] Patent Number: 5,849,558
[45] Date of Patent: Dec. 15, 1998

[54] DISCOVERY OF AND METHOD FOR CLONING AND PRODUCING THE PSPGI RESTRICTION ENDONUCLEASE

[75] Inventors: Richard D. Morgan, Middleton, Mass.; Zhiyuh Chang, New Rochelle, N.Y.

[73] Assignee: New England Biolabs, Inc., Beverly, Mass.

[21] Appl. No.: 856,663

[22] Filed: May 15, 1997

[51] Int. Cl.$^6$ .............................. C12N 15/55; C12N 9/22
[52] U.S. Cl. ................. 435/199; 435/252.33; 435/320.1; 536/23.2
[58] Field of Search ............................... 435/199, 252.33, 435/320.1; 536/23.2

[56] References Cited

U.S. PATENT DOCUMENTS 5,200,333   4/1993   Wilson .

OTHER PUBLICATIONS

Kosykh et al., Molec. Gen. Genet., 178:717–718 (1980).
Mann et al., Gene, 3:97–112 (1978).
Walder et al., Proc. Nat. Acad. Sci., 78:1503–1507 (1981).
Bougueleret et al., Nucl. Acid Res., 12:3659–3676 (1984).
Gingeras and Brooks, Proc. Natl. Acad. Sci. USA 80:402–406 (1983).
Theriault and Roy, Gene, 19:355–359 (1982).
Blumenthal et al., J. Bacteriol., 164:501–509 (1985).
Kiss et al., Nucl. Acid Res., 13:6403–6421 (1985).
Szomolanyi et al, Gene, 10:219–225 (1980).
Janulaitis et al., Gene, 20:197–204 (1982).
Kiss and Baldauf, Gene, 21:111–119 (1983).
Walder et al., (J. Biol. Chem., 258:1235–1241 (1983).
Piekarowicz et al., Nucleic Acid Res. 19:1831–1835 (1991).
Piekarowicz et al., J. Bacteriology, 173:150–155 (1991).
Fomenkov et al., Nucleic Acids Res. 22:2399–2403 (1994).
Lunnen et al., Gene, 74:25–32 (1988).
Raleigh and Wilson, Proc. Natl. Acad. Sci, USA, 83:9070–9074 (1986).
Heitman and Model, J. Bact., 196:3243–3250 (1987).
Raleigh et al., Genetics, 122:279–296 (1989).
Waite–Rees et al., J. Bacteriology, 173:5207–5219 (1991).
Sanger et al. Proc. Natl. Acad. Sci., 74:5463–5467 (1977).
Brown et al., J. Mol. Biol. 140:143–148 (1980).
Fuller, Gene 19:43–54 (1982).
Shimatake and Rosenberg, Nature, 292:128 (1981).
Shine & Dalgarno, Proc. Natl. Acad. Sci. USA, 71:1342–1346 (1974).
Ikemura, J. Mol. Biol., 151:389–409 (1981).
Matsudaira, J. Biol. Chem. 262:10035–10038 (1987).
Looney, et al., Gene 80:193–208 (1989).
Birnboin and Doly, Nucl. Acids Res. 7:1513 (1973).

*Primary Examiner*—Charles L. Patterson, Jr.
*Attorney, Agent, or Firm*—Gregory D. Williams

[57] ABSTRACT

The present invention relates to the type II restriction endonuclease PspGI, obtainable from Pyrococcus species G-I-H (NEB #906), an enzyme which recognizes the DNA sequence 5' CC(A/T)GG 3' and cleaves before the first C of the recognition sequence to produce a 5 base 5' extension:

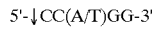

5'-↓CC(A/T)GG-3'

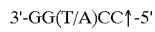

3'-GG(T/A)CC↑-5'

(wherein G represents guanine, C represents cytosine, A represents adenine and T represents thymine and (A/T) represents either A or T in that one position.)

8 Claims, 2 Drawing Sheets

DISCOVERY OF AND METHOD FOR CLONING AND PRODUCING THE PSPGI RESTRICTION ENDONUCLEASE

BACKGROUND OF THE INVENTION

The present invention relates to discovery and identification of the PspGI restriction endonuclease, obtainable from Pyrococcus species G-I-H (NEB#906) and to the process for producing the same, and to the recombinant DNA which encodes the PspGI restriction endonuclease and modification methylase, and the production of PspGI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTTAAA, PuGGNCCPy and CACNNNGTG, respectively. *Escherichia coli* RY13, on the other hand, synthesizes only one enzyme, EcoRI, which recognizes the sequence GMTTC.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always modified by virtue of the activity of its modification methylase. It is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12:3659–3676, (1984); PaeR7: Gingeras and Brooks, *Proc. Natl. Acad. Sci. USA* 80: 402–406, (1983); Theriault and Roy, *Gene* 19:355–359 (1982); PvuII: Blumenthal et al., *J. Bacteriol.* 164:501–509, (1985)).

A third approach which is being used to clone a growing number of systems, involves selection for an active methylase gene (refer to U.S. Pat. No. 5,200,333 and BsuRI: Kiss et al., *Nucl. Acid. Res.* 13:6403–6421, (1985). Since restriction and modification genes are often closely linked, both genes can often be cloned simultaneously. This selection does not always yield a complete restriction system however, but instead yields only the methylase gene (BspRI: Szomolanyi et al., *Gene* 10:219–225, (1980); Bcn I: Janulaitis et al, *Gene* 20:197–204 (1982); Bsu RI: Kiss and Baldauf, *Gene* 21:111–119, (1983); and Msp I: Walder et al., *J. Biol. Chem.* 258:1235–1241, (1983)).

Another method for cloning methylase and endonuclease genes is based on a calorimetric assay for DNA damage. When screening for a methylase, the plasmid library is transformed into the host *E. coli* strain such as AP1-200. The expression of a methylase will induce the SOS response in an *E. coli* strain which is McrA$^+$, McrBC$^+$, or Mrr$^+$. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et. al., *Nucleic Acids Res.* 19:1831–1835, (1991) and Piekarowicz, et. al. *J. Bacteriology* 173:150–155 (1991)). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the abscence of it's cognate methylase when the endonuclease damages the host cell DNA, inducing the SOS response. The SOS-induced cells form deep blue colonies on LB agar plates supplemented with X-gal. (Fomenkov et. al. *Nucleic Acids Res.* 22:2399–2403 (1994)).

Sometimes the straight-forward methylase selection method fails to yield a methylase (and/or endonuclease) clone due to various obstacles. See, e.g., Lunnen, et al., Gene, 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems lies in the discovery that some strains of E. coli react adversely to cytosine or adenine modification; they possess systems that destroy DNA containing methylated cytosine (Raleigh and Wilson, Proc. Natl. Acad. Sci., USA 83:9070–9074, (1986)) or methylated adenine (Heitman and Model, J. Bact. 196:3243–3250, (1987); Raleigh, et al. Genetics, 122:279–296, (1989) Waite-Rees, et al., J. Bacteriology, 173:5207–5219 (1991)). Cytosine-specific or adenine-specific methylase genes cannot be cloned easily into these strains, either on their own, or together with their corresponding endonuclease genes. To avoid this problem it is necessary to use mutant strains of E. coli (McrA$^-$ and McrB$^-$ or Mrr$^-$) in which these systems are defective.

A third potential difficulty is that some restriction endonuclease and methylase genes may not express in E. coli due to differences in the transcription machinery of the source organism and E. coli, such as differences in promotor and ribosome binding sites. The methylase selection technique requires that the methylase express well enough in E. coli to fully protect at least some of the plasmids carrying the gene.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY OF THE INVENTION

The present invention relates to the type II restriction endonuclease PspGI, obtainable from Pyrococcus species G-I-H (NEB #906), an enzyme which recognizes the DNA sequence 5' CC(A/T)GG 3' and cleaves before the first C of the recognition sequence to produce a 5 base 5' extension:

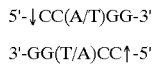

(wherein G represents guanine, C represents cytosine, A represents adenine and T represents thymine and (A/T) represents either A or T in that one position.)

The present invention also relates to recombinant DNA encoding the genes for the PspGI restriction endonuclease and modification methylase obtainable from Pyrococcus species G-I-H as well as related methods for the production of these enzymes from the recombinant DNA. This invention also relates to a transformed host which expresses the restriction endonuclease PspGI. PspGI restriction endonuclease produced according to the present invention is substantially pure and free of the contaminants normally found in restriction endonuclease preparations made by conventional techniques.

DETAILED DESCRIPTION OF THE INVENTION

Figure 1:
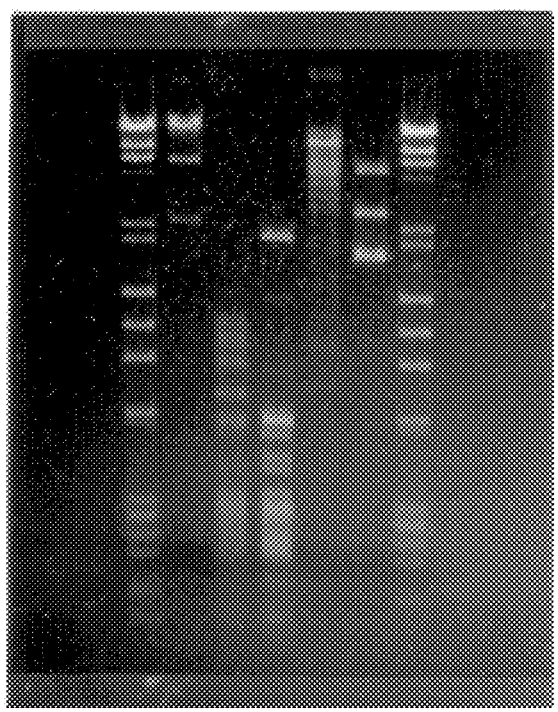
FIG. 1 illustrates the PspGI cleavage pattern of various DNAs. PspGI restriction endonuclease was purified from Pyrococcus species G-I-H strain NEB#906. 2 units of the purified PspGI restriction endonuclease was used to digest 0.5 g of DNA in 30 ul of reaction volume in 1× NEBuffer III. The reactions were incubated at 65° C. for 1 hour. Lanes 1 and 7: HindIII-λ+HaeIII-φ174 size standard; lane 2: PspGI digest of T7 DNA; lane 3: PspGI digest of Adeno2 DNA; lane 4: PspGI digest of Adeno2-pUC19 BC4 dcm− DNA; lane 5: PspGI digest of Adeno2-pUC19 BC4 dcm+ DNA; lane 6: PspGI digest of pUC19 dcm+ DNA.

In accordance with one embodiment of the present invention, PspGI may be obtained by culturing Pyrococcus species G-I-H strain NEB#906 and recovering the endonuclease from the cells. A sample of Pyrococcus species G-I-H NEB#906 has been deposited at the American Type Culture Collection (ATCC) on Jan. 30, 1998 and bears the Accession Number 202084.

For recovering the enzyme of the present invention from the native strain (rather than the clone), P. species G-I-H may be grown using any suitable technique. For example, P. species G-I-H may be grown in a media comprised of 0.5× difco marine broth mixed with an equal volume of difco sea salts (40 g/L) plus 0.01M cysteine plus 0.005M BTP plus 10 g/L sulfur, which is incubated at 85° C. in flasks without aeration or agitation. Cells in the late logarithmic stage of growth are collected by centrifugation and either disrupted immediately or stored frozen at −70° C.

The PspGI enzyme can be isolated from P. species G-I-H cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing PspGI. The PspGI endonuclease is then purified from the cell-free extract by ion-exchange chromatography, affinity chromatography, molecular sieve chromatography, or a combination of these methods to produce the endonuclease of the present invention.

The endonuclease of the present invention, along with its corresponding methylase, may also be obtained using recombinant DNA techniques.

The methylase selection method (U.S. Pat. No. 5,200, 333) was attempted, though not exhaustively, to obtain a PspGI methylase producing clone. An E. coli strain which was lacking the dcm methylase system was used, since PspGI is blocked by dcm methylation and thus the dcm methylase would prevent selection against non-PspGI methylase producing clones. The attempts made to clone PspGI by methylase selection failed. An attempt to clone PspGI by the endo blue selection method also failed. Instead it was decided to use the highly purified PspGI restriction endonuclease protein obtained from P. species G-I-H cells to determine amino acid sequence at the N-terminus of the endonuclease. The amino acid sequence was then used to design degenerate oligonucleotide primers for PCR amplification of this region of DNA from genomic P. species G-I-H DNA. The sequence of the small PCR amplified DNA was then used to design non-degenerate inverse PCR primers, which were used to amplify DNA flanking the start of the PspGI endonuclease gene. This DNA was sequenced and the sequence data was used to design primers to PCR amplify the intact endonuclease gene from genomic P. species G-I-H DNA for insertion into a suitable expression vector.

The preferred method for cloning the PspGI restriction-modification system consists of purifying the PspGI endonuclease to near homogeneity and determining the amino acid sequence at the N-terminus of the protein. The DNA coding for this N-terminal region of the PspGI endonuclease is amplified using degenerate oligonucleotide primers based on the protein sequence. DNA adjacent to the N-terminal portion of the PspGI endonuclease is then amplified by inverse PCR techniques, cloned and sequenced. The PspGI endonuclease can then be expressed by amplifying the complete gene from Pyrococcus species G-I-H DNA and cloning it into an expression vector such as pRRS or pAII17. This construct is introduced into a host which is premodified at PspGI sites either by virtue of the PspGI methylase gene carried on a separate compatible plasmid or the E. coli dcm methylase. PspGI endonuclease is produced by growing the host containing the PspGI endonuclease and methylase genes, or the PspGI endonuclease and E. coli dcm methylase genes, inducing with the appropriate expression conditions, harvesting the cells and purifying the PspGI endonuclease.

The recognition sequence of the endonuclease of the present invention may be determined by mapping the locations of PspGI cleavage in various DNAs and comparing the DNA sequences of these regions for homology. The endonuclease PspGI was found to cleave T7 phage DNA in two places. These cut sites were mapped to approximate positions of 2400 and 8200 by simultaneously digesting T7 DNA with PspGI and with endonucleases which cleave at known positions, such as MluI, Bg/II, NruI, StuI, EcoNI, ApaLI and BstBI. The sequence CC(A/T)GG occurs in T7 DNA at positions 2366 and 8188. PspGI was found to not cleave pUC19 DNA, pBR322 DNA and φX174 DNA grown in a dcm methylase producing host. Very little amount of cleavage was observed when substrate Adeno2-pUC19 BC4 DNA (a DNA construct made by inserting the BstBI 10670 to ClaI 18657 fragment of Adeno2 DNA into AccI 429 site on pUC19 DNA) grown in a dcm methylase producing host was used. This lack of cleavage occurred because the sites for PspGI in these DNAs were methylated by the E. coli dcm methylase, which methylates at the same CC(A/T)GG sequence which PspGI recognizes (New England Biolabs 1996/1997 catalog, pg. 243). PspGI did cut un-methylated pUC19 DNA, pBR322 DNA and Adeno2-pUC19 BC4 DNA grown in a dcm-minus host, producing the size fragments expected for cleavage at CC(A/T)GG. The size of fragments produced by PspGI cleavage of Adeno2 DNA and SV40 DNA, both of which are not methylated at CC(A/T)GG, is consistant with cleavage at CC(A/T)GG (FIG. 1). From this evidence we conclude that PspGI recognizes the sequence CC(A/T)GG. PspGI differs from BstNI, which also recognizes CC(A/T)GG, in that PspGI is much more thermostable, is sensitive to dcm methylation (BstNI is not sensitive to dcm methylation), and PspGI cleaves at a different position in the recognition sequence. PspGI differs from EcoRII in that PspGI is much more thermostable, and the PspGI methylase has homology to the $m^4C_\alpha$-methylases, whereas EcoRII methylase is a $m^5C$-methylase.

The point of cleavage within the PspGI recognition sequence may be determined through dideoxy sequencing analysis of the terminal base sequence obtained from PspGI cleavage of a suitable DNA substrate (Sanger, et al., *Proc. Natl. Acad. Sci*, 74:5463–5467 (1977), Brown, et al., *J. Mol. Biol.* 140:143–148 (1980).). By the above referenced method it was found that PspGI cleaves the phosphodiester bond preceding the 5' most C of the recognition sequence CC(AIT)GG to produce a five base 5' extension, as indicated by the arrows:

$$5'\text{-}\downarrow CC(A/T)GG\text{-}3'$$
$$3'\text{-}GG(T/A)CC\uparrow\text{-}5'$$

The enzyme of the present invention also has the following properties:

(a) Optimal buffer composition: The optimal buffer tested was NEBuffer III, supplemented with 100 ug/ml bovine serum albumin. Relative activity in NEBuffer I was 10%, in NEBuffer II was 80% and in NEBuffer IV was 25%.

(b) Heat Inactivation: 1 unit of PspGI in 100 ul NEBuffer III can not be inactivated in twenty minutes at 65° C.

(c) Enzyme Stability: 0.125 unit of PspGI is required to cleave 1 ug Lambda phage DNA in 50 uls NEBuffer III to completion in sixteen hours at 65° C.

(d) Heat Stability: PspGI has a half-life of 6 hours at 95° C. in 1× NEB ThermoPol buffer.

(e) PspGI has a molecular weight of approximately 31 kD as determined by polyacrylamide gel electrophoresis.

(f) Amino terminal PspGI protein sequence: Amino acid sequence at the amino terminus of the purified 31 kD PspGI protein was obtained. The sequence of the first 28 residues, correlated with subsequent DNA sequence at the start of the endonuclease gene, was the following: MVRNLVIDI TKKPTQNIPPTNEIIEEAI (SEQ ID NO: 1).

The method described herein by which the PspGI restriction endonuclease and methylase genes are preferably cloned and expressed includes the following steps:

1. Pyrococcus species G-I-H is grown in flasks containing the media described above at 85° C., the cells are harvested, lysed and the genomic DNA purified.

2. The PspGI restriction endonuclease is purified to near homogeniety from Pyrococcus species G-I-H cells by a combination of protein purification techniques developed at New England Biolabs, Inc. (Beverly, Mass.) (see Example 1, step 2). The endonuclease so purified is nearly homogeneous on SDS polyacrylamide gel electrophoresis and has an apparent molecular weight of approximately 31 kilodaltons.

3. The amino terminal amino acid sequence of the endonuclease is obtained using an Applied BioSystems Division, Perkin-Elmer Corporation (Foster City, Calif.) 470A Protein Sequencer (Waite-Rees, et al., *J. Bacteriol.* 173:5207–5219 (1991)), and used to direct synthesis of degenerate oligonucleotide primers for amplification of the DNA at the start of the PspGI endonuclease gene from Pyrococcus species G-I-H genomic DNA, and to identify the PspGI endonuclease gene in subsequent studies.

4. A portion of the PspGI endonuclease gene is amplified using two degenerate DNA primers, one corresponding to the amino acid sequence near the start of the gene (amino acids 4 to 10) and one corresponding to the amino acid sequence further downstream in the gene (amino acids 21 to 27) for the reverse strand of DNA.

5. The amplified DNA obtained from step 4 is cloned into pUC19 and sequenced. The DNA sequence obtained for the region between the two degenerate primers is used to design non-degenerate oligonucleotide primers oriented outward toward the unknown DNA flanking the amplified DNA of step 4 in order to inverse PCR amplify the flanking DNA.

6. Pyrococcus species G-I-H genomic DNA is digested by ApoI, HpaII and AciI endonucleases and the resulting fragments are ligated at low DNA concentration to favor intramolecular ligation. The circularized fragments containing DNA corresponding to the N-terminus of the PspGI endonuclease gene are amplified using two synthetic primers which anneal to the known sequence region and are oriented with their 3' ends toward the unknown region. The ApoI digested and circularized DNA produces a 0.55 kb product, the HpaII digested and circularized DNA produces a 2.3 kb product, and the AciI digested and circularized DNA yields a 1.8 kb product.

7. The amplified DNAs containing regions flanking the amino-terminal region of the endonuclease gene are cloned into pUC19 and sequenced. An open reading frame coding for amino acid sequence that matches the N-terminal amino acid sequence of the endonuclease is observed, and is the correct size to produce a protein of approximately 31 kD. The AciI product contains 1.15 kb of sequence 5' to the start of the endonuclease. The HpaII product contains 0.3 kb of sequence 5' to the endonuclease gene and 1.2 kb of sequence 3' to the endonuclease gene. An open reading frame containing amino acid sequences corresponding to conserved motifs of $m^4C_{60}$-methylases is observed 3' to the endonuclease gene. This open eading frame is believed to be the PspGI methylase.

8. Overexpressing the PspGI endonuclease gene:

A. General considerations:

There are a number of ways in which the restriction gene can be overexpressed. The DNA sequence and detailed mapping information help determine the best approach for overexpression of the restriction endonuclease gene.

One approach for overexpression comprises designing primers that hybridize directly at the N-terminus of the restriction endonuclease gene and somewhere downstream (3') of the gene in order to use the polymerase-chain reaction to amplify the entire endonuclease gene. The resulting DNA fragment can be inserted into an expression vector such as pRRS directly downstream of an inducible promoter (lacUV5).

Alternatively, overexpression can be accomplished by inserting a promoter recognized strongly by E. coli, such as Ptac on pAGR3 (New England Biolabs, Inc.; Beverly, Mass.) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the Ptac promoter. Other regulated promoters which can be used are PlacUV5 (Fuller, Gene 19:43–54 (1982)), and IPL (Shimatake and Rosenberg, Nature 254:128 (1981)) on pUC19 and pBR322 derivatives. In addition, a strong ribosome binding site (Shine & Dalgarno, Proc. Natl. Acad. Sci. USA 71:1342–1346 (1974)) can be placed in front of the gene to increase expression.

To obtain a stable clone which overexpresses the restriction endonuclease, the host is generally pre-protected from restriction endonuclease digestion. In the present invention this is accomplished by cloning the PspGI endonuclease into an E. coli host carrying the dcm methylase. Alternatively, a host which does not carry the dcm methylase may be preprotected from PspGI digestion by cloning the PspGI methylase on a separate plasmid. The plasmid used must be compatible with the expression vector. The methylase also must be produced at a level which will protect the host's genome from digestion by the overexpressed restriction endonuclease gene.

The DNA sequence of the gene can be altered by site-directed mutagenesis or by resynthesizing the gene itself to use codons that are more efficiently utilized in E. coli (Ikemura, J. Mol. Biol. 151:389–409 (1981)).

B. Expression of PspGI endonuclease:

DNA primers are designed and synthesized to amplify the entire PspGI endonuclease gene. The forward primer has the following elements: a PstI cloning site, stop codon in frame with the lacZ gene, E. coli consensus strong ribosome binding site, 7 nucleotide spacer sequence between the ribosome binding site and the ATG start codon of the PspGI endonuclease, a change of codon usage in amino acid number 3 to an E. coli preferred codon and 20 nucleotides matching the PspGI endonuclease DNA sequence for hybridization. The 3' primer is designed to hybridize Pyrococcus species G-I-H DNA approximately 70 bp beyond the 3' end of the endonuclease gene. BamHI and SalI sites were introduced in the reverse primer to facilitate cloning. The endonuclease gene is amplified from the genomic DNA using these primers. The amplified DNA is cleaved by PstI and BamHI and ligated into the expression vector pRRS, which has been previously cleaved by the same enzymes and gel purified. The ligation reaction is transformed into E. coli ER2502 competent cells and grown at 30° C. Clones producing the PspGI endonuclease are identified by growing streaking individual colonies onto a master plate, then growing pools of ten clones overnight in 10 ml LB, followed by the addition of 27 ml LB, growth for 1 hour, addition of IPTG to 0.5 mM with growth at 37° C. for two hours, after which the cells are harvested and assayed for the presence of PspGI endonuclease activity. One pool tested was found to have activity and the individual clone producing PspGI was identified by the same method. One such PspGI expressing host, designated PspGIR70, is propagated and used to produce PspGI restriction endonuclease.

Figure 2:
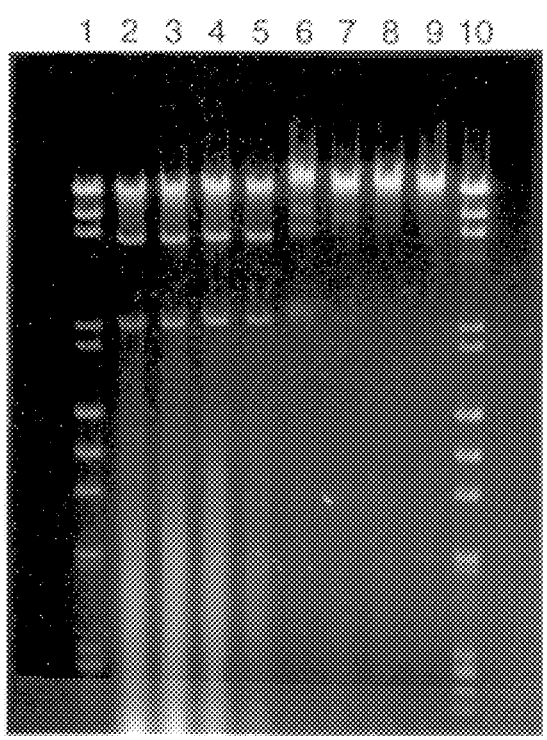
FIG. 2 is a photograph of an agarose gel demonstrating PspGI restriction endonuclease activity in cell extracts of E. coli ER2502 carrying the PspGI endonuclease on the pRRS derived plasmid pPspGIR70. 1 gram of cells was suspended in 10 ml of sonication buffer (20 mM Tris-HCl, 1 mM Dithiothreitol, 0.1 mM EDTA, 50 mM NaCl, pH 7.5) and broken by sonication. The extract was used to digest 1 ug of T7 DNA per 50 ul reaction volume in 1× NEBuffer III. The reactions were incubated at 65° C. for 1 hour. Lanes 1 and 10: HindIII-λ+HaeIII-φX174 size standard; lane 2: 4 μl crude extract; lane 3: 2 μl crude extract; lane 4: 1 μl crude extract; lane 5: 0.5 μl crude extract; lane 6: 0.25 μl crude extract; lane 7: 0.125 μl crude extract; lane 8: 0.0625 μl crude extract; lane 9: 0.031 μl crude extract.

9. Production: The PspGI endonuclease may be produced from host cells carrying the overexpressed PspGI restriction endonuclease gene by propagation in a fermenter in a rich medium with the appropriate antibiotic selection and induction. The cells are thereafter harvested by centrifugation and disrupted by sonication to produce a crude cell extract containing approximately 20,000 $\mu$/g of PspGI restriction endonuclease activity assayed on T7 DNA (FIG. 2).

10. Purification: The crude cell extract containing the PspGI endonuclease is purified by a combination of protein purification techniques, such as affinity-chromatography or ion-exchange chromatography.

Although the above-outlined steps represent the preferred mode for practicing the present invention, it will be apparent to those skilled in the art that the above described approach can vary in accordance with techniques known in the art.

The following Example is given to illustrate embodiments of the present invention as it is presently preferred to practice. It will be understood that this Example is illustrative, and that the invention is not to be considered as restricted thereto except as indicated in the appended claims.

The references cited above and below are incorporated by reference.

EXAMPLE

Cloning the PspGI Restriction Endonuclease Gene

1. DNA purification:

To prepare the genomic DNA of Pyrococcus species G-I-H (NEB #906), 2 g of cell paste was resuspended by gentle shaking in 20 ml of 25% sucrose, 0.05M Tris-HCl, 1 mM EDTA, pH 8.0. 5 ml of 0.5M EDTA, pH 8.0 and 6 ml of freshly prepared 10 mg/ml lysozyme in 0.25M Tris-HCl pH 8.0 was added and the solution was incubated at 4° C. for 2 hours. 24 ml of Lysis mix (1% Triton-X100, 50 mM Tris, 62.5 mM EDTA, pH 8.0) was added followed by 5 ml of 10% SDS and the solution was incubated at 4° C. overnight. The solution was extracted with 50 ml of equilibrated phenol, the aqueous phase was recovered and extracted with 50 ml of chloroform two times. The aqueous solution was dialysed against four changes of 2 L of 10 mM Tris, 1 mM EDTA, pH 8.0 overnight. The dialysed solution was then digested with RNase (100 ug/ml) at 37° C. for 1 hour. The DNA was precipitated by the addition of 1/10th volume 5M NaCl and 0.55 volume of 2-propanol and spooled onto a glass rod. The DNA was air dried and then dissolved in 10 ml of 10 mM Tris, 1 mM EDTA, pH 8.0.

2. Purification of the PspGI restriction endonuclease from Pyrococcus species G-I-H to near homogeneity:

Pyrococcus species G-I-H (NEB#906) cells were propagated in a media comprised of 0.5× difco marine broth mixed with an equal volume of difco sea salts (40 g/L) plus 0.01M cysteine plus 0.005M BTP plus 10 g/L sulfur and incubated at 85° C. in flasks without aeration or agitation. Cells in the late logarithmic stage of growth were collected by centrifugation and stored at −70° C. until used. All of the following procedures were performed on ice or at 4° C. 10 g of cell pellet (wet weight) was resuspended in 35 ml of buffer A.1 (20 mM Tris-HCl, 1 mM Dithiothreito (DTT), 0.1 mM EDTA, 0.1M NaCl, pH 7.5) and broken by sonication. The extract was centrifuged at 15,000 rpm for 15 minutes at 4° C. The supernatant was loaded onto a 20 ml heparin-sepharose column equilibrated with buffer A.1. The column was washed with 60 ml of buffer A.1, followed by a 200 ml linear gradient from 0.1M NaCl to 1M NaCl in buffer A (20 mM Tris-HCl, 1 mM Dithiothreitol (DTT), 0.1 mM EDTA, pH 7.5). 5 ml fraction were collected. Fractions were assayed for PspGI restriction activity with T7 DNA and the peak of restriction enzyme activity was found to elute from the column between 0.38 to 0.45M NaCl and was pooled. The amount of PspGI endonuclease was estimated to be 25,000 units. This heparin-sepharose pool was diluted with 2 volumes of buffer A and applied to a 3 ml heparin-TSK FPLC column (TosoHaas; Philadelphia, Pennsylvania) equilibrated in buffer A.1, followed by a 40 ml linear gradient of 0.1M NaCl to 0.6M NaCl in buffer A. 1 ml fractions were collected. Fractions were assayed for PspGI activity with T7 DNA. The peak of restriction enzyme activity eluted between 0.35 and 0.45 M NaCl and 8 fractions were pooled. This heparin-TSK pool contained approximately 10,000 units PspGI activity. The pool was diluted with 4 volumes of buffer A and loaded onto a 1 ml Mono Q FPLC column (Pharmacia: Piscataway, N.J.) equilibrated with Buffer A containing 60 mM NaCl (A.06), washed with 6 ml of buffer A.06 and then a 40 ml linear gradient from 0.1M NaCl to 0.6M NaCl in Buffer A was formed. 1 ml fractions were collected. Fractions were assayed for PspGI activity with T7 DNA. The PspGI activity eluted between 0.20 and 0.23M NaCl and 2 fractions were pooled.

This Mono Q pool was diluted with 4 volumes buffer A and loaded onto a 1 ml Mono S FPLC column (Pharmacia: Piscataway, New Jersey) equilibrated with buffer A.06, washed with 6 ml of buffer A.06 followed by a 40 ml linear gradient from 0.1M NaCl to 0.6M NaCl in buffer A. 1 ml fractions were collected. Fractions were assayed for PspGI activity with T7 DNA. All of the enzyme activity eluted with the wash and was pooled. This Mono S pool was loaded onto a 1 ml PolyCat A FPLC column (Pharmacia: Piscataway, N.J.) equilibrated in buffer A.06 followed by a 40 ml linear gradient of 0.1M NaCl to 0.6M NaCl in buffer A. 1 ml fractions were collected. Fractions were assayed for PspGI activity with T7 DNA. The enzyme activity eluted in the wash and first 10 fractions. The polycat A pool was diluted with an equal volume of buffer A and loaded onto the MonoQ FPLC column again and treated as above. Approximately 2,000 units of PspGI activity was purified to near homogeneity. 16 µl of the peak fraction was loaded onto an SDS-PAGE protein gel and subjected to electrophoresis. The gel was stained with Coomassie blue R-250 and a prominent band at approximately 31 kD corresponding to the PspGI restriction endonuclease activity was observed.

3. Amino Terminal PspGI protein sequence:

The PspGI restriction endonuclease, prepared as described in section 2 above, was subjected to electrophoresis and electroblotted according to the procedure of Matsudaira (Matsudaira, *J. Biol. Chem.* 262:10035–10038 (1987)), with modifications as previously described (Looney, et al., *Gene* 80:193–208 (1989)). The membrane was stained with Coomassie blue R-250 and the protein band of approximately 31 kd was excised and subjected to sequential degradation on an Applied BioSystems Division, Perkin-Elmer Corporation (Foster City, Calif.) Model 407A gas phase protein sequencer (Waite-Rees, et al. *J. Bacteriol.* 173:5207–5219 (1991)). The first 28 residues of the 31 kd protein corresponded to (Met)-Val-Arg-Asn-Leu-Val-Ile-Asp-Ile-Thr-Lys-Lys-Pro-Thr-Gln-Asn-Ile-Pro-Pro-Thr-Asn-Glu-Ile-Ile-Glu-Glu-Ala-Ile (SEQ ID NO: 2).

4. Amplification of N-terminal PspGI DNA:

Two degenerate primers were designed based on the amino acid sequence information. The forward primer, based on amino acids 4 to 10 (NLVIDIT (SEQ ID NO: 3), had the following sequence: PspGI-P1: 5' GTTGGATCC-MCCTNGTNATHGAYATHAC 3' (SEQ ID NO: 4). The reverse primer, based on amino acids 21 to 27 (NEIIEEA (SEQ ID NO: 5), had the following sequence: PspGI-P2: 5' GTTCTGCAGGCYTCRTADATDATYTCRTT 3' (SEQ ID NO: 6). This reverse primer was later found to contain mismatches to the actual PspGI DNA sequence, but it was successful in amplifying the PspGI endonuclease target. In the reaction that was successful in amplifying the product, a reaction mix was made by combining:

10 ul of 10× Vent™ reaction buffer 6 ul of 4 mM dNTP solution 5 ul of primer PspGI-P1 at 10 uM concentration 5 ul of primer PspGI-P2 at 10 uM concentration 4 ul of 100 mM MgSO$_4$ (6 mM Mg$^{++}$ final concentration)

1 ul of PspGI genomic DNA (approximately 100 ng)

69 ul dH$_2$O 2 ul (4 units) of Vent™ Exo$^-$ polymerase NEB#257

The PCR amplification conditions were: 95° C. for 3 minutes for one cycle, followed by 4 cycles of 95° C. for 20 seconds, 38° C. for 30 seconds and 72° C. for 5 seconds, followed by 20 cycles of 95° C. for 20 seconds, 56° C. for 30 seconds and 72° C. for 5 seconds. 10 ul of the PCR reaction was analyzed by electrophoresis on a 3% NuSieve agarose gel.

5. Cloning and Sequencing the N-terminal portion of the PspGI endonuclease:

The amplified product of step 4 was electrophoresed in a 3% NuSieve agarose gel and excised. The DNA was purified from the gel by digesting the agarose with β-Agarase (NEB #392) according to the manufacturers instructions. The purified DNA was cleaved with BamHI (NEB#136) and PstI (NEB#140), the endonucleases were heat inactivated at 78° C. for 15 minutes and the DNA was ligated to pUC19 vector previously cleaved with the same endonucleases and dephosphorylated. The ligation product was transformed into E. coli ER2426 and the DNA of individual transformants was checked for the presence of the insert by performing minipreps and digesting with PstI and BamHI.

Analysis of plasmid clones:

Individual transformants were inoculated into 1.8 ml cultures of L-broth containing ampicillin and the plasmids that they carried were prepared by the following miniprep plasmid purification procedure, adapted from the method of Birnboin and Doly (*Nucleic Acids Res.* 7:1513 (1973)).

Miniprep Procedure:

1.5 ml of each culture was centrifuged at 8000 rpm for 2 minutes; the supernatant was discarded and the cell pellet was resuspended in 200 µl of 25 mM Tris, 10 mM EDTA, 50 mM glucose, pH 8.0. 400 µl of a freshly prepared solution of 0.2M NaOH, 1% SDS was added to each tube and the tubes were shaken to lyse the cells. Once the solutions had cleared, 300 µl of 3M Na Acetate pH 4.8 was added to each and gently mixed by shaking. The precipitates that formed were spun down at 14,000 rpm at 4° C. for 3 minutes. Each supernatant was poured into a centrifuge tube containing 700 µl of isopropanol and mixed. The tubes were spun at 14,000 rpm at 4° C. for 5 minutes to pellet the precipitated nucleic acids. The supernatants were discarded and the pellets were air-dried at room temperature for 15 minutes. Once dried, the pellets were dissolved in 250 µl of 10 mM Tris pH 8.0, 1 mM EDTA, containing 50 µg/ml RNase and incubated for 1 hour at 37° C. to digest the RNA. The DNA was precipitated by the addition of 25 µl of 5M NaCl followed by 175 µl of 2-propanol. The DNA was collected by centrifugation for 5 minutes at 4° C., the supernatants were discarded, the pellets were dried and then redissolved in 50 µl of 10 mM Tris, 1 mM EDTA pH 8.0 (1× TE). The plasmid minipreps were subsequently analyzed by digestion with various restriction enzymes.

DNA sequencing of the amplified PspGI DNA plasmids was performed using an ABI 373 automated DNA sequencer according to the manufacturer's instructions, using pUC19 universal sequencing primers (NEB#1224 and NEB#1233). Once DNA sequence information was obtained, the amino acid sequence translated from the DNA sequence was compared with the amino acid sequence obtained directly from the PspGI endonuclease protein. The DNA sequence between the primers was found to be 5'-(AC)MAGAMCCAACACAAAACATTCCTCCA ACA-3' (SEQ ID NO: 7), which translates into the amino acid sequence: TKKPTQNIPPT (SEQ ID NO: 8), which matches the amino acid sequence call. Two non-degenerate primers based on this sequence information were synthesized in order to amplify DNA adjacent to this N-terminal region of the PspGI endonuclease gene from genomic Pyrococcus species G-I-H DNA using inverse PCR methods. These primers had the sequence: PspGI-IP1: 5' GTTGGATCCCAAMACAT-TCCTCCAAC 3' (SEQ ID NO: 9).

PspGI-IP2: 5' GTTCTGCAGTTGTGTTGGTTTCTTTG 3' (SEQ ID NO: 10)

6. Cloning DNA adjacent to the PspGI endonuclease amino terminal region:

Template preparation for inverse PCR amplification: 1 ug of Pyrococcus species G-I-H DNA was digested with 10 units of HpaII restriction endonuclease in 1× NEBuffer #2 in a 50 ul reaction volume for 1 hour at 37° C. The HpaII enzyme was heat inactivated by incubating at 75° C. for 20 minutes. The HpaII digested DNA was circularized by adding 50 ul 10× T4 DNA ligase buffer and 400 ul dH₂O, followed by 5 ul (2000 NEB units) T4 DNA ligase (NEB #202) and incubating at 16° C. for 16 hours. A portion of this circularization ligation reaction was then used as the template for subsequent inverse PCR reactions. Circularized ApoI and AciI digested Pyrococcus species G-I-H DNA was prepared in the same manner.

Primers PspGI-IP1 and PspGI-IP2 of sequences shown above were used to amplify DNA adjacent to the start of the PspGI endonuclease. In the reaction that was successful in amplifying the product, a reaction mix was made by combining:

10 ul of 10× Vent™ reaction buffer 6 ul of 4 mM dNTP solution 5 ul of primer PspGI-IP1 at 10 uM concentration 5 ul of primer PspGI-IP2 at 10 uM concentration 4 ul of 100 mM MgSO₄ (6 mM Mg⁺⁺ final concentration)

12.5 ul of circularized DNA template (approximately 25 ng)

58 ul dH₂O 2 ul (4 units) of Vent™ Exo⁻ polymerase NEB#257

The PCR amplification conditions were: 95° C. for 3 minutes for one cycle, followed by 4 cycles of 95° C. for 20 seconds, 48° C. for 30 seconds and 72° C. for 2 minutes, followed by 20 cycles of 95° C. for 20 seconds, 62° C. for 30 seconds and 72° C. for 2 minutes. 10 ul of the PCR reaction was analyzed by electrophoresis on a 0.8% agarose gel.

A 0.55 kb product was observed in the ApoI circular template PCR reaction, a 1.8 kb product was observed in the AciI circular template PCR reaction, and a 2.3 kb product was observed in the HpaII circular template PCR reaction. These three products were gel purified and resuspended in 25 ul 1× TE. These PCR products were then sequenced using an ABI 373 automated sequencing system according to the manufacturer's instructions, using the PCR primers above as the sequencing primers.

7. Cloning and sequencing DNA adjacent to the start of the PspGI endonuclease:

The 1.8 kb AciI and 2.3 kb HpaII products were cloned into pUC19 by digesting with PstI and BamHI, which cut at the end of the primers, and cloning into pUC19 vector previously cleaved with BamHI and PstI. Minipreps were performed to identify plasmid clones carrying the desired inserts. The complete sequence of these clones was obtained by subcloning portions of the cloned DNA, using HindIII, EcoRI, SacI and SmaI, to effectively move the universal pUC sequencing primers close to the various parts of the DNA. An open reading frame coding for amino acid sequence that matched the N-terminal amino acid sequence of the endonuclease was observed, and 816 bp/272 amino acids was of a size that is consistent to produce a protein of approximately 31 kD. The AciI product contained 1.15 kb of sequence 5' to the start of the endonuclease. The HpaII product contained 0.3 kb of sequence 5' to the endonuclease gene and 1.2 kb of sequence 3' to the endonuclease gene. An open reading frame containing amino acid sequences corresponding to conserved motifs of $m^4$-$C_\alpha$-methylases was observed 3' to the endonuclease gene. This open reading frame is believed to be the PspGI methylase. By comparison with MvaI and BspHI methylases, it is estimated that approximately 40 or 50 amino acids (120 to 150 bp) of sequence at the amino terminus of the PspGI methylase remained to be cloned. The PspGI methylase amino acid sequence at motif I is: MMIPQVARKSIKL-WGKNAKVILDPFCGSG TVLVEAKIKNI NSYGFD (SEQ ID NO: 11), where the bold characters match the consensus sequence for $m^4C_\alpha$-methylases. The PspGI methylase amino acid sequence at motif IV is: DLILTSP-PYGD (SEQ ID NO: 12), where the bold characters match the consensus sequence for $m^4C_\alpha$-methylases.

8. Endonuclease cloning:

The restriction endonuclease gene was expressed by inserting the gene into an expression vector, pRRS, directly downstream of a strong inducible promotor (PlacUV5) and a strongly recognized ribosome binding site. To accomplish this, two oligonucleotide primers were made utilizing the DNA sequence data. The forward oligonucleotide primer contained a PstI (and NdeI) site to facilitate cloning, a stop codon in frame with the lacZ gene to terminate translation of the lacZ protein, a strongly recognized ribosome binding site, seven nucleotide spacer between the rbs and the ATG start codon of the PspGI endonuclease gene, a change of codon usage in amino acid three to an E. coli preferred codon (from AGA to CGT) and 20 nucleotides complementary to Pyrococcus species G-I-H DNA for hybridization:

Primer PspGIRexp1: 5'-GTTCTGCAGATMGGAGGTTAAACATA TGGTTCGTAATCTCGTTATTGATATAAC-3' (SEQ ID NO: 13)

The reverse primer was designed to hybridize to Pyrococcus species G-I-H DNA 70 bp beyond the 3' end of the PspGI endonuclease gene. It contained a BamHI (and SalI) restriction site to facilitate cloning and 20 nucleotides complementary to Pyrococcus species G-I-H DNA for hybridization:

Primer PspGIRexp2: 5'-CAAGGATCCGTCGACAAATAA-GAGAAT GCCCCAC 3' (SEQ ID NO: 14)

These two primers were used to amplify the PspGI endonuclease gene from Pyrococcus species G-I-H genomic DNA by combining:

10 ul 10× Vent™ reaction buffer
6 ul of 4 mM dNTPs
1 ul (100 ng) Pyrococcus species G-I-H genomic DNA
5 ul (10 uM stock) primer PspGIRexp1
5 ul (10 uM stock) primer PspGIRexp2
4 ul of 100 mM $MgSO_4$
69 ul $dH_2O$
0.8 ul (1.6 units) Vent™ polymerase (2 unit/ul stock)

and amplifying at 95° C. for 3 minutes for 1 cycle, followed by 4 cycles of 95° C. for 30 seconds, 56° C. for 20 seconds, 72° C. for 45 seconds, followed by 20 cycles of 95° C. for 30 seconds, 64° C. for 20 seconds and 72° C. for 45 seconds. The amplification product of approximately 850 bp was gel purified, cleaved with PstI and BamHI, phenol-chloroform extracted, precipitated, resuspended in TE and ligated into pRRS vector previously cleaved with PstI and BamHI and gel purified. The ligation reaction was transformed into E. coli strain ER2502, which carries the E. coli dcm methylase, by electroporation. Out of 244 individual transformants analyzed, one expressed PspGI endonuclease activity. This clone, pPspGIR70, was selected for producing the PspGI endonuclease and given the strain designation of NEB #1096. A titration of the PspGI restriction endonuclease activity produced from crude extracts of NEB #1096 is shown in FIG. 2. The enzyme titer was approximately $2 \times 10^4$ units/g of cells.

9. The PspGI restriction endonuclease may be produced from NEB #1096 by propagation to mid-log phase in a fermenter containing L-broth medium with ampicillin (100 μg/ml) and kanamycin (50 μg/ml). The culture is induced by the addition of IPTG to a final concentration of 0.3 mM and allowed to continue growing for 16 hours. The cells are harvested by centrifugation and may be stored at −70° C. or used immediately.

10. Purification of the PspGI restriction endonuclease from NEB #1096 can be accomplished by a combination of standard protein purification techniques, such as affinity-chromatography or ion-exchange chromatography, as outlined in step 2 above. The PspGI restriction endonuclease obtained from this purification is substantially pure and free of non-specific endonuclease and exonuclease contamination.

A sample of the E. coli strain ER2502 containing pPspGIR70 (NEB#1096) has been deposited under the terms and conditions of the Budapest Treaty with the American Type Culture Collection on May 15, 1997, and received ATCC Accession Number 98435.

What is claimed is:

1. Isolated DNA coding for the PspGI restriction endonuclease, wherein the isolated DNA is obtainable from Pyrococcus species G-I-H.

2. A recombinant DNA vector comprising a vector into which a DNA segment coding for the PspGI restriction endonuclease has been inserted.

3. Isolated DNA coding for the PspGI restriction endonuclease and methylase, wherein the isolated DNA is obtainable from ATCC No. 98435.

4. A cloning vector which comprises the isolated DNA of claim 3.

5. A host cell transformed by the cloning vector of claims 2 or 4.

6. A method of producing a PspGI restriction endonuclease comprising culturing a host cell transformed with the vector of claim 2 or 4 under conditions suitable for expression of said endonuclease.

7. A substantially pure Type II restriction endonuclease endogenous to Pyrococcus species G-I-H recognizing the following base sequence in double-stranded deoxyribonucleic acid molecules:

$$5'\text{-}\downarrow CC(A/T)GG\text{-}3'$$

$$3'\text{-}GG(T/A)CC\uparrow\text{-}5'$$

and having a cleavage position defined by the arrows.

8. A method for obtaining Type II restriction endonuclease of claim 7, comprising cultivating a sample of Pyrococcus species G-I-H under conditions favoring production of said endonuclease and separating said endonuclease therefrom.

* * * * *

UNITED STATES PATENT AND TRADEMARK OFFICE
CERTIFICATE OF CORRECTION

PATENT NO. : 5,849,558  
DATED : December 15, 1998  
INVENTOR(S) : Morgan, et al Page 1 of 2

It is certified that error appears in the above-identified patent and that said Letters Patent is hereby corrected as shown below:

Column 1, line 38, replace "GMTTC" with --GAATTC--

Column 2, line 44, replace "calorimetric" with --colorimetric--.

Column 5, line 48, replace "Bg/II" with --*Bgl*II--

Column 6, line 18, replace "CC(AIT)GG" with --CC(A/T)GG--

Column 7, line 39, replace "$m^4C_{60}$" with -- $m^4C_\alpha$ --

Column 10, line 50, replace "MCCTN" with --AACCTN--

Column 11, line 62, replace "MAGAMCC" with --AAAGAAACC--

Column 12, line 3, replace "GTTGGATCCCAAMACAT" with --GTTGGGATCCCAAAACAT--

Column 13, line 16, replace "QVARKSIKL" with --QVARKSIKL--

Column 13, line 17, replace "VILDPFCGSG TVLVEAKIKNI NSYGFD" with VILDPFCGSG TVLVEAKIKNINSYGFD

Column 13, line 20-21, replace "DLILTSP-PYGD" with --DLILTSPPYGD--

Column 13, line 40, replace "GTTCTGCAGATM" with --GTTCTGCAGATAA--

UNITED STATES PATENT AND TRADEMARK OFFICE
CERTIFICATE OF CORRECTION

PATENT NO. : 5,849,558
DATED : December 15, 1998
INVENTOR(S) : Morgan, et al

It is certified that error appears in the above-identified patent and that said Letters Patent is hereby corrected as shown below:

Column 9, line 42, replace "Dithiothreito" with --Dithiothreitol--

Column 10, line 59, replace "Vent™" with --Vent®--

Column 10, last line, replace "Vent™" with --Vent®--

Column 12, line 29, replace "Vent™" with --Vent®--

Column 12, line 39, replace "Vent™" with --Vent®--

Column 14, line 4, replace "Vent™" with --Vent®--

Column 14, line 12, replace "Vent™" with --Vent®--

Signed and Sealed this

Fourteenth Day of September, 1999

Attest:

Q. TODD DICKINSON

*Attesting Officer*   *Acting Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single ( D ) TOPOLOGY: linear ( i i ) MOLECULE TYPE: protein ( x i ) SEQUENCE DESCRIPTION: SEQ ID NO:1:

| Met | Val | Arg | Asn | Leu | Val | Ile | Asp | Ile | Thr | Lys | Lys | Pro | Thr | Gln | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Pro | Pro | Thr | Asn | Glu | Ile | Ile | Glu | Glu | Ala | Ile |
|-----|-----|-----|-----|-----|-----|-----|-----|-----|-----|-----|-----|
|     |     |     | 20  |     |     |     |     | 25  |     |     |     |

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

| Met | Val | Arg | Asn | Leu | Val | Ile | Asp | Ile | Thr | Lys | Lys | Pro | Thr | Gln | Asn |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ile | Pro | Pro | Thr | Asn | Glu | Ile | Ile | Glu | Glu | Ala | Ile |
|-----|-----|-----|-----|-----|-----|-----|-----|-----|-----|-----|-----|
|     |     |     | 20  |     |     |     |     | 25  |     |     |     |

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

| Asn | Leu | Val | Ile | Asp | Ile | Thr |
|-----|-----|-----|-----|-----|-----|-----|
| 1   |     |     |     | 5   |     |     |

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY:
        ( B ) LOCATION: 15...15
        ( D ) OTHER INFORMATION: N=G, A, C or T (U)
        ( A ) NAME/KEY:
        ( B ) LOCATION: 18...18
        ( D ) OTHER INFORMATION: N=G, A, C or T (U)
        ( A ) NAME/KEY:
        ( B ) LOCATION: 21...21
        ( D ) OTHER INFORMATION: H = A or C or T (U)
        ( A ) NAME/KEY:
        ( B ) LOCATION: 27...27
        ( D ) OTHER INFORMATION: H = A or C or T (U)
        ( A ) NAME/KEY:
        ( B ) LOCATION: 24...24
        ( D ) OTHER INFORMATION: Y = C or T(U)

( x i ) SEQUENCE DESCRIPTION: SEQ ID NO:4:

GTTGGATCCA ACCTNGTNAT HGAYATHAC 29

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

Asn Glu Ile Ile Glu Glu Ala
1               5

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY:
        ( B ) LOCATION: 12...12
        ( D ) OTHER INFORMATION: Y=C or T (U)
        ( A ) NAME/KEY:
        ( B ) LOCATION: 24...24
        ( D ) OTHER INFORMATION: Y=C or T (U)
        ( A ) NAME/KEY:
        ( B ) LOCATION: 15...15
        ( D ) OTHER INFORMATION: R=A or G
        ( A ) NAME/KEY:
        ( B ) LOCATION: 27...27
        ( D ) OTHER INFORMATION: R=A or G
        ( A ) NAME/KEY:
        ( B ) LOCATION: 18...18
        ( D ) OTHER INFORMATION: D=G or A or T (U)
        ( A ) NAME/KEY:
        ( B ) LOCATION: 21...21
        ( D ) OTHER INFORMATION: D=G or A or T (U)

( x i ) SEQUENCE DESCRIPTION: SEQ ID NO:6:

GTTCTGCAGG CYTCRTADAT DATYTCRTT        29

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:7:

ACAAAGAAACC AACACAAAAC ATTCCTCCAA CA        33

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

Thr Lys Lys Pro Thr Gln Asn Ile Pro Pro Thr
1               5               10

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:9:

GTTGGATCCC AAAACATTCC TCCAAC                        26

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:10:

GTTCTGCAGT TGTGTTGGTT TCTTTG                        26

( 2 ) INFORMATION FOR SEQ ID NO:11:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met  Met  Ile  Pro  Gln  Val  Ala  Arg  Lys  Ser  Ile  Lys  Leu  Trp  Gly  Lys
 1             5                        10                       15
Asn  Ala  Lys  Val  Ile  Leu  Asp  Pro  Phe  Cys  Gly  Ser  Gly  Thr  Val  Leu
               20                       25                       30
Val  Glu  Ala  Lys  Ile  Lys  Asn  Ile  Asn  Ser  Tyr  Gly  Phe  Asp
          35                       40                       45
```

( 2 ) INFORMATION FOR SEQ ID NO:12:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Asp  Leu  Ile  Leu  Thr  Ser  Pro  Pro  Tyr  Gly  Asp
 1             5                        10
```

( 2 ) INFORMATION FOR SEQ ID NO:13:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:13:

GTTCTGCAGA TAAGGAGGTT AAACATATGG TTCGTAATCT CGTTATTGAT ATAAC    55

( 2 ) INFORMATION FOR SEQ ID NO:14:

( i ) SEQUENCE CHARACTERISTICS:
       ( A ) LENGTH: 34 base pairs
       ( B ) TYPE: nucleic acid
       ( C ) STRANDEDNESS: single
       ( D ) TOPOLOGY: linear ( i i ) MOLECULE TYPE: Genomic DNA ( x i ) SEQUENCE DESCRIPTION: SEQ ID NO:14:

CAAGGATCCG TCGACAAATA AGAGAATGCC CCAC    34